(12) United States Patent
Settineri et al.

(10) Patent No.: US 9,205,070 B2
(45) Date of Patent: Dec. 8, 2015

(54) CHELATION SUPPOSITORY FOR IMPROVED DRUG DELIVERY

(71) Applicant: APPLIED BIORESEARCH, INC., Draper, UT (US)

(72) Inventors: Robert A. Settineri, Irvine, CA (US); Ernest H. Pfadenhauer, Santa Barbara, CA (US)

(73) Assignee: APPLIED BIORESEARCH, INC., Draper, UT (US)

( * ) Notice: Subject to any disclaimer, the term of this patent is extended or adjusted under 35 U.S.C. 154(b) by 0 days.

(21) Appl. No.: 14/206,915

(22) Filed: Mar. 12, 2014

(65) Prior Publication Data

US 2014/0275258 A1 Sep. 18, 2014

Related U.S. Application Data

(60) Provisional application No. 61/778,256, filed on Mar. 12, 2013, provisional application No. 61/943,143, filed on Feb. 21, 2014.

(51) Int. Cl.
*A61K 9/02* (2006.01)
*A61K 31/198* (2006.01)

(52) U.S. Cl.
CPC .................................. *A61K 31/198* (2013.01)

(58) Field of Classification Search
CPC .............................. A61K 9/02; A61K 31/198
USPC .......................... 424/436, DIG. 15; 514/965
See application file for complete search history.

(56) References Cited

U.S. PATENT DOCUMENTS

| | | | |
|---|---|---|---|
| 4,873,087 A | 10/1989 | Morishita | |
| 6,309,663 B1 | 10/2001 | Patel | |
| 2003/0216479 A1 | 11/2003 | Huang | |
| 2004/0265344 A1* | 12/2004 | Zolotariov | A61K 9/02 424/400 |
| 2007/0173515 A1* | 7/2007 | Chang et al. | 514/255.04 |
| 2008/0159984 A1 | 7/2008 | Ben-Sasson | |
| 2009/0068168 A1* | 3/2009 | Gant et al. | 424/94.64 |

OTHER PUBLICATIONS

MSDS for CANa2-EDTA from BASF 2012.*
Ellithorpe et al, Nov. 5, 2010, Detoxamin.*
(Detoxamin EDTA Chelation Suppositories, http://www.peak-health-now.com/detoxamin-EDTA-chelation-suppositories-ingredients.html.*
International Search Report and Written Opinion of International Application No. PCT/US2014/024927 mailed Aug. 11, 2014.
Ellithrope, R. et al, (Reprint p. 1-7) "Comparison of the Absorption, Brain and Prostate Distribution, and Elimination of CaNa2 EDTA of Rectal Chelation Suppositories to Intravenous Administration", JANA, 2007, vol. 10, No. 2, pp. 38-44.

* cited by examiner

*Primary Examiner* — Blessing M Fubara
(74) *Attorney, Agent, or Firm* — Koppel, Patrick, Heybl & Philpott; Michael J. Ram

(57) ABSTRACT

Described herein is a method of delivering drugs to the blood stream directly by absorption through cell membranes in the wall of the rectum from a rectal suppository comprising a glyceride based excipient More specifically, $CaNa_2$ EDTA is delivered rectally from a suppository containing water soluble, glyceride based excipient/carrier.

12 Claims, No Drawings

US 9,205,070 B2

CHELATION SUPPOSITORY FOR IMPROVED DRUG DELIVERY

This application claims benefit of U.S. Provisional Application 61/778,256 filed Mar. 12, 2013 and U.S. Provisional Application 61/943,143 filed Feb. 21, 2014.

FIELD OF THE INVENTION

This invention is directed to compositions for providing an excipient delivery system for negatively-charged drugs, particularly calcium disodium ethylenediaminetetraacetate ($CaNa_2EDTA$) to enhance absorption of the drug through living cell membranes as well as interstitial cell spaces. Negatively charged (anionic) drugs are poorly absorbed across cell membranes if they become solvated in water, such as body fluids including, but not limited to, saliva, gastric juices, colonic fluid, nasal, vaginal, mucosal, interstitial fluids and rectal fluid. Because anionic drugs are less permeable through biological membranes, these drugs are commonly administered by intravenous drip, intraperitoneal injections, intranasal instillation, inhalation therapy or subcutaneous injection. These methods are invasive and painful, and can be expensive.

BACKGROUND

Drug absorption is typically predicted based on tests designed to evaluate oral administration. There are several distinct steps in modeling or understanding drug absorption including release from the excipient; solvation in the body fluid; absorption by the luminal or mucosal cells and distribution to local or systemic sites. (Shono Y, Jantratid E, Kesisoglou F, Reppas C, Dressman J B. "Forecasting in vivo oral absorption and food effect of micronized and nanosized aprepitant formulations in humans." *Eur J Pharm Biopharm.* pp 95-104 September; 76(1), (2010))

The first step is the release of the drug from the excipient or carrier. This is universally tested by dissolution. The drug and excipient combination are chosen to dissolve in the target body fluid. For instance, a sublingual delivery would be optimized to dissolve in saliva, while a stomach delivery would be designed to be released in the acidic milieu of the gastric juices. Enteric coatings that are designed to resist dissolution in an acidic environment are used to deliver drugs to the small intestine. Suppositories are designed to dissolve in the rectal fluid (or to melt), for example from hydrophobic carriers such as cocoa butter, fatty acids or hydrogenated vegetable oils Oral delivery systems include tablets, gel capsules and capsules. These can contain excipients such as binders (e.g., hydroxypropylmethylcellulose, polyvinyl pyrilodone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc).

Transmucosal delivery systems include patches, tablets, suppositories, pessaries, gels and creams, and can contain excipients such as solubilizers and enhancers (e.g. propylene glycol, bile salts and amino acids), and other vehicles (e.g., polyethylene glycol, fatty acid esters and derivatives, and hydrophilic polymers such as hydroxypropylmethylcellulose and hyaluronic acid).

Dermal delivery systems include, for example, aqueous and nonaqueous gels, creams, multiple emulsions, microemulsions, liposomes, ointments, aqueous and nonaqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer.

SUMMARY

MBK, and more particularly MBK in a fatty acid base, is a preferred excipient for thorough and consistent release of $CaNa_2$ EDTA from a rectal suppository. The $CaNa_2$ EDTA was dissolved or suspended in the delivery means, and the permeability of the drug was tested for the appropriate target. Cells in the digestive track, such as CACO-2 cells are typically used to model absorption in the small intestine. CACO-2 cells, developed by the Sloan-Kettering Institute from human epithelial colorectal adenocarcinoma cells, are widely used to predict drug absorption. Parallel absorption membrane permeability assay (PAMPA) uses an artificial cell membrane to model drug permeability. In either test, the drug is dissolved in an aqueous solution mimicking the target gastric fluid. The fluid is contacted with the membrane, and the passage of the drug through the membrane over a period of time is used to assess permeability.

However, a better method of estimating human bioavailability is to administer the drug in a chosen formulation to an animal (for example, a rat) and comparing the blood levels to the same drug administered intravenously. The conclusive measure of bioavailability is to measure the drug blood levels (or levels in some other body fluid) after administration to human test subjects.

DETAILED DISCUSSION

A particular anionic drug, namely EDTA and more particularly calcium disodium ethylenediaminetetraacetate ($CaNa_2EDTA$), is FDA-approved for treatment of lead poisoning via intravenous administration and the utility for this purpose has been recently reconfirmed. (Born T, Kontoghiorghe C N, Spyrou A, Kolnagou A, Kontoghiorghes G J. "EDTA chelation reappraisal following new clinical trials and regular use in millions of patients: review of preliminary findings and risk/benefit assessment.", *Toxicol Mech Methods*. January; 23(1):11-7(2013). However, numerous attempts to provide more convenient oral delivery have failed.

It has been found by applicants from animal studies that delivery of EDTA via a suppository comprising PCCA Base MBK™, described in the literature as a hydrophobic excipient comprising methylbutylketone in hydrogenated vegetable oil and peg-8 distearate or in a fatty acid base, is successful. Administration via suppository of $CaNa_2EDTA$ with MBK as the excipient (see Table 1) allowed over 36.3% of the drug to be absorbed within eight hours in a rat pharmacokinetic model. Table 1 is data showing bioavailability of $CaNa_2EDTA$ delivered from a suppository using a rat animal model compared to IV delivery. However, prior studies using an aqueous solution have shown that a much lower absorption is found in dogs (~13%,) and a highly variable and lesser absorption was noted in humans when the EDTA is administered rectally. See Rabau M Y, Baratz M, Rozen P, "$Na_2$ ethylenediaminetetraacetic acid retention enema in dogs. Biochemical and histological response". *Gen Pharmacol.*; 22(2): 329-30. (1991) for rectal delivery and Elia M, Behens C, Northrop C, Wraight P, Neale G: Evaluation of mannitol, lactulose and 51Cr-labeled ethylenediaminetetra-acetate as markers of intestinal permeability in man. See *Clinical Science* 1987; August 73(2):197-204 regarding intestinal permeability in humans.

Likewise, orally administered enteric-coated EDTA, which provides EDTA to the higher pH environment in the small intestine, is not well absorbed. Enteric coatings, which consist, for example, of polymers that are resistant to dissolving in stomach acid but release the drug in the higher pH of the small intestine or colon can be provided in an attempt to avoid the acidic environment of the stomach. Hall E J, Batt R M, Brown A., "Assessment of canine intestinal permeability, using 51Cr-labeled ethylenediaminetetraacetate." *Am J Vet Res.* December; 50(12): 2069-74 (1989)

However, studies have shown that while the hPAT1 transporter is readily found in the small intestine, it is not found in particular abundance in the colon or rectum. (Broberg M I, Holm R, Tønsberg H, Frølund S, Ewon K B, Nielsen A I, Brodin B, Jensen A, Kall M A, Christensen K V, Nielsen C U "Function and expression of the proton-coupled amino acid transporter PAT1 along the rat gastrointestinal tract: implications for intestinal absorption of gaboxadol." *Br J Pharmacol.* October; 167(3):654-65 (2012))

The conclusion was reached that it was possible that the good bioavailability observed in the rat study was due to the direct transfer of $CaNa_2EDTA$ from the hydrophobic MBK excipient to the mucosal cells in the rectum.

TABLE 1

Bioavailability and Pharmacokinetics of $CaNa_2EDTA$ Rectal Suppository vs IV Administration in Rats

| Group | Route | Stat. | Dose (mg/kg) | AUC (µg × Hr/mL) | AUC Inf (µg × Hr/mL) | Halflife (Hour) | Cmax (µg/ml) | Tmax (Hour) | Absolute Bioavailability (%) |
|---|---|---|---|---|---|---|---|---|---|
| B | Intravenous | MEAN | 1.37 | 1.86 | 1.91 | 1.50 | 2.07 | 0.083 | N/A |
|   |   | SD | 0.06 | 0.20 | 0.19 | 0.34 | 0.35 | 0.000 |   |
|   |   | N | 4 | 4 | 4 | 4 | 4 | 4 |   |
| C | Rectal | MEAN | 213.5 | 105.8 | 307.3 | 8.20[1] | 30.6 | 0.417 | 36.3 |
|   |   | SD | 12.0 | 32.2 | 225.6 | 5.61 | 10.6 | 0.144 |   |
|   |   | N | 3 | 3 | 3 | 3 | 3 | 3 |   |

$$\text{Absolute bioavailability}(\%) = \frac{(AUC_{test} \times Dose_{ref})}{(AUC_{ref} \times Dose_{ref})} \times 100$$

Where "test" data is the rectal data, and "ref" (reference) data is the intravenous data.
[1]The terminal elimination phase was not observed, therefore, this calculation is interpolated and longer sample intervals should be examined.

An explanation for the poor gastric absorption of EDTA can be the behavior of calcium disodium EDTA or disodium EDTA solvated in water at different pHs. EDTA has six different acid dissociation constants ($pK_a$), causing it to be strongly ionic and thus highly water soluble at higher pHs. (Coleman, William F. "Molecular Models of EDTA and Other Chelating Agents", (*Journal of Chemical Education*, Vol. 85 No. 9 September (2008)

However, at lower pHs, EDTA becomes only very sparingly soluble. It is believed that this causes orally ingested EDTA to precipitate in stomach acid and is thus lost from further bioavailability. Enteric coating will protect the EDTA from stomach acid, but the solvation of the highly hydrophilic drug in the gastric fluid will still cause it to be resistant to absorption.

In the second stage of modeling drug absorption, PAMPA tests were run at pH 7.0 and pH 9.6 in anticipation of optimizing a suppository delivery system for $CaNa_2$ EDTA. PAMPA measures how quickly the drug can exit a water-solvated environment and pass through a cell membrane. Since most drugs are hydrophobic, it is expected that there will be significant absorption by the cells lining the digestive tract.

However, it was suspected that the PAMPA tests might be negative for $CaNa_2EDTA$ in an aqueous composition containing MBK based on the highly hydrophilic nature of the drug. The results of those PAMPA tests were indeed completely negative; no drug was found to have passed through the artificial cell membrane after 5 hours of testing. Test results were validated by use of low and high control drugs, Atenolol and Verapamil, respectively.

The possibility that a protein amino acid transporter, hPAT1, was responsible for higher-than-expected absorption rate with the suppository route of delivery was then evaluated.

It is known that cell permeability for small molecular weight drugs is highest for non-ionic drugs and decreases as the drug is more neutral and there is lesser amount of transport for negatively charged drugs. It is further known that hydrophobic drugs are more easily absorbed than hydrophilic drugs. Since $CaNa_2EDTA$ is both anionic and hydrophilic it is therefore postulated that the mechanism for increasing absorption was by direct transfer from the hydrophobic MBK excipient to the mucosal cells.

To prepare the suppository, the $CaNa_2EDTA$ in its crystalline form was mixed with an equal weight of MBK in a fatty acid base, melted cocoa butter or other excipient as described herein at about 50° C. The excipients comprising MBK in the fatty acid base or cocoa butter are non-ionic, or uncharged (not negatively charged). Other inert solids, such as Methocel® (methylcellulose and hydroxypropyl methylcellulose polymers) may be included. The composition was formed into a rectal suppository of a typical size used for rectal delivery of prior art materials. The suppository of comprises from about 100 mg to about 1.2 gm of $CaNa_2EDTA$ or an EDTA salt such as a Na, Mg or Fe salt delivering an equivalent amount of EDTA. In a particular embodiment, these suppositories contain about 50% of the MBK fatty acid component or other excipient and about 50% of $CaNa_2EDTA$. In a preferred embodiment the suppository contains about 600 milligrams of the excipient and about 600 milligrams of $CaNa_2EDTA$.

A typical human rectal suppository is a conical or torpedo shaped item about 2-3 centimeters in length. Suppositories for adults weigh about 2-3 grams each; suppositories for children weigh about 1-2 grams each. The typical carriers used are waxy materials in which the active ingredients have been dissolved or suspended. While the MBK in the fatty acid base may constitute a suitable carrier, other carriers including, but not limited to, glycerin, glyceryl monopalmitate, glyceryl monostearate, hydrogenated coconut oil fatty acids, cocoa butter, and hydrogenated palm kernel oil fatty acids can be used.

Example 1

To prepare a suppository the $CaNa_2EDTA$ in its crystalline form was mixed with an equal weight of MBK in a fatty acid carrier or melted cocoa butter at about 50° C., the MBK component or cocoa butter excipients being non-ionic, or uncharged (not negatively charged). Other inert solids, such as Methocel® (methylcellulose and hydroxypropyl methylcellulose polymers) may be included. The composition was then formed into a rectal suppository of typical size containing about 600 milligrams of excipient and about 600 milligrams of $CaNa_2EDTA$.

Example 2

A comparative study was conducted to evaluate the accessibility of $CaNa_2EDTA$ to systemic circulation in a mammalian body by measuring the amount of excreted EDTA in the pooled urine of mammalian test subjects collected for two time periods (0-8 hrs and 8-24 hours) after rectal insertion of an EDTA containing suppository and rectal retention thereof for at least 80 minutes. Cumulative excretion was calculated by adding the EDTA amounts from the two time periods, and correcting for any EDTA present in urine before administration of the suppository. The EDTA urine analysis was performed by LC/MS/MS using heavy isotope labeled EDTA as an internal standard. The efficacy of delivering EDTA was compared for 5 different excipients, namely MBK in the fatty acid base, polyethylene glycol (PEG), Witepsol H12, Witespol W45, and Suppocire AIML. The procedure was repeated 3 days later using an EDTA suppository with a different excipient. The percentage of EDTA accounted for in urine from the various formulations is shown in Table 2.

The MBK excipient is described above. The other excipients are as described below.

WITEPSOL® WITEPSOL H12® and WITEPSOL W45® are Hydrogenated Coco-Glycerides available from Cremer Oleo GmbH & Co. KG, Glockengiesserwall 3, 20095 Hamburg, Germany. WITEPSOL H grades are hard fats with a low hydroxyl value of max. 15 and comprise mainly triglycerides with proportions of max. 15% of diglycerides and max. 1% of monoglycerides. H12 has a melting point of about 32-33.5° C. and a hydroxyl value of 5-15 mg KOH/g WITEPSOL W grades are hard fats with hydroxyl values between 20-50. They comprise a mixture of 65-80% of triglycerides, 10-35% of diglycerides and 1-5% of monoglycerides. W45 has a melting point of about 33-35.5° C. and a hydroxyl value of 40-50 mg KOH/g.

PEG-Dow Chemical offers several polyethylene glycol compounds which are water soluble and have various molecular weights known as Carbowax® Sentry. The preferred PEG selected for the comparative study was PEG 1450 also referred to as Carbowax® Sentry1450 as described below with a molecular weight range of 1305-1595.

Suppocire AIML®—Semi-synthetic glyceride base comprising saturated C8-C18 triglyceride fatty acids and a phospholipid additive (lecithin) with a low hydroxyl value available from Gattefossé with headquarters in Saint-Priest, Lyon.

TABLE 2

EDTA URINE CONCENTRATIONS FROM SUPPOSITORY DELIVERY

| EXCIPIENT | SAMPLE | TOTAL mg 0-24 HRS |
|---|---|---|
| MBK | 1 | 8.63 |
|  | 2 | 0.5 |
|  | 3 | 6.25 |
|  | 4 | 3.63 |
| AVG mg |  | 4.75 |
| % of ADMINISTERED |  | 0.6% |
| RSD |  | 74% |
| PEG 1450 | 5 | 31.07 |
|  | 6 | 4.53 |
|  | 2 | 26.32 |
|  | 7 | 71.76 |
| AVG |  | 33.42 |
| % of ADMINISTERED |  | 4.5% |
| RSD |  | 84% |
| WITEPSOL H12 | 5 | 123.77 |
|  | 8 | 38.31 |
|  | 9 | 80.24 |
|  | 3 | 21.93 |
| AVG |  | 66.06 |
| % of ADMINISTERED |  | 8.8% |
| RSD |  | 69% |
| WITEPSOL W45 | 10 | 68.22 |
|  | 8 | 14.85 |
|  | 6 | 43.22 |
|  | 7 | 43.91 |
| AVG |  | 42.55 |
| % of ADMINISTERED |  | 5.7% |
| RSD |  | 51% |
| SUPPOCIRE AIML | 1 | 73.89 |
|  | 10 | 48.81 |
|  | 9 | 84.38 |
|  | 4 | 35.13 |
| AVG |  | 60.56 |
| % of ADMINISTERED |  | 8.1% |
| RSD* |  | 37% |

*Relative Standard Deviation

Contrary to initial expectations that MBK in a fatty acid base would provide superior transport directly through the cell membrane it was discovered that water soluble polar excipients appear to provide better transport of the $CaNa_2EDTA$ and are therefore expected to provide elevated concentrations of the EDTA in the blood for superior heavy metal chelation. In particular Suppocire AIML and Witepsol H12, were the most effective, with Witepsol W45 being effective to a lesser extent. These compounds are all glyceride based compounds. PEG 1450, even though it is water soluble, was beneficial but to a less effective extent. MBK provided an EDTA transport of less than about 8% of the two most effective excipients and only about 14% of the transport provided by PEG 1450.

A typical rectal suppository is a conical or torpedo shaped item about 2-3 centimeters in length. Suppositories for adults

| Products | Form | Molecular Weight Range | Average Number of Repeating Oxyethylene units | CTFA Nomenclature | Density (20° C.) | Density (60° C.) | Melting at Freezing Range | Solubility in Water at 20° C., % by wt | Viscosity at 100° C. |
|---|---|---|---|---|---|---|---|---|---|
| CARBOWAX SENTRY 1450 | Solid | 1305-1595 | 32.5 | PEG-32 | Solid at specified Temperature | 1.0919 | 42 to 45 | 72 | 26.5 | weigh about 2-3 grams each; children suppositories weigh about 1-2 grams each. The typical carriers used are waxy materials in which the active ingredients have been dissolved or suspended. The carrier can comprise, but is not limited to, glycerin, glyceryl monopalmitate, glyceryl monostearate, hydrogenated coconut oil fatty acids, cocoa butter, and hydrogenated palm kernel oil fatty acids.

The same result could be achieved by allowing the drug to dissolve in the body fluid and adjusting the pH. However, this could cause precipitation and loss of bioavailability as discussed above. As a result, the direct transfer of the non-ionic drug from the excipient-containing suppository to the absorbing cells allows the correct and advantageous optimization and delivery of hydrophilic anionic drugs.

The above process bypasses the traditional concept of solvation of the drug into the surrounding body fluid and is dependent on the contact of the $CaNa_2EDTA$-MBK containing composition directly with the absorbing cells. Mass transfer of the drug through the excipient to the cell membrane is assumed to occur through diffusion in light of the small volume of rectal fluid present (about 3 ml with a pH of about 7.5) compared to the volume of a typical suppository (also about 3 ml for adults).

This composition disclosed herein can be used to better define molecular models; better design and choose excipients that interact with absorbing cells and exclude water; and re-design PAMPA and CACO-2 analyses to test permeability of a drug in a hydrophobic medium versus an aqueous medium. Other dosage forms that will benefit from this new understanding of hydrophilic drug absorbance are identified herein.

In addition, solutions, suspensions and powders for reconstitutable delivery systems include vehicles such as suspending agents (e.g., gums, zanthans, cellulosics and sugars), humectants (e.g., sorbitol), solubilizers (e.g., ethanol, water, PEG and propylene glycol), surfactants (e.g., sodium lauryl sulfate, Spans, Tweens, and cetyl pyridine), preservatives (e.g. parabens) and antioxidants (e.g., vitamins E and C, and ascorbic acid), anti-caking agents, coating agents, and chelating agents other than EDTA.

MBK was used in prior work and considered to allow fairly good absorption of the drug. However, the MBK was in a fatty base and the addition of methyl cellulose does not appear to change its functional characteristics. As the fatty base slowly melts at body temperature (melting point between 30 and 37 degrees), it may not release the drug rapidly for good absorption. In fact, some of the drug may be so intimately bound to the base that it does not release at all.

In contrast, PEG is a completely water soluble base and melts and dissolves to release the drug readily. However, the drug is poorly permeable and, although released in the rectal fluid, may not be readily absorbed.

The Witepsol and Suppocire bases are triglycerides (fatty bases) with some mono- and di-glycerides which act as emulsifying agents. Thus at least some of the fatty base is emulsified. The emulsion contains water and oil in intimate contact and in this physical form, the drug is allowed to permeate the rectal issues. While the exact mechanism of permeation enhancement is not known, it is believed that the emulsion allows and intimate contact of oil and water and provides the best environment for the absorption of the drug.

PEG provided a better bioavailability than the MBK composition because the PEG is hydrophilic and does not retard release of the drug while the MBK hydrophobic base does retard release. The Witepsol and Suppocire bases form emulsions, in part, thus facilitating absorption. Witepsol W45 displayed better bioavailability than PEG, and Witepsol H12 showed better bioavailability than the W45 grade. The Suppocire product contains lecithin as an emulsifying agent (in addition to mono- and di-glycerides), thus providing a similar effect.

Although Suppocire displayed slightly lower bioavailability than Witepsol H12, the relative standard deviation value of the bioavailability data from individual subjects (RSD) receiving Suppocire were significantly lower for this incipient.

To further enhance the solubilization, absorption and transport of the EDTA compound, the $CaNa_2$ EDTA or any alternative EDTA compounds that are used, can be micronized or nanosized. Traditional micronization techniques are based on friction to reduce particle size to a few microns in diameter. Nano-sized particles are a few nanometers in size. Such methods include milling, bashing and grinding. Alternatively the EDTA salts can initially be crystallized as micron-sized or nano-sized crystals. Published literature has shown that nanoparticles, because of their size, can increase the potential for the nanosized material to crossing the various biological barriers within the body, in particular the blood brain and can allow access into the cell and various cellular compartments including the nucleus.

While the above described products are suppositories, the formulations provided above can be utilized for transdermal delivery of the EDTA compounds or delivery through other mucus membranes such as buccal contacting delivery systems.

We claim:

1. A suppository for use in chelating heavy metals in a living being comprising:
   i. calcium disodium ethylenediaminetetraacetate ($CaNa_2$ EDTA),
   ii. an excipient comprising from 65% to 80% triglycerides, and
   iii. a carrier comprising one or more of glycerin, glyceryl monopalmitate, glyceryl monostearate, hydrogenated coconut oil fatty acids, cocoa butter, and fatty acids.

2. The suppository of claim 1 wherein the triglycerides form an emulsion with calcium disodium ethylenediaminetetraacetate.

3. The suppository of claim 2 including an emulsifying agent.

4. The suppository of claim 3 wherein the excipient further comprises diglycerides, the diglycerides acting as emulsifying agents.

5. The suppository of claim 3 wherein the excipient comprises triglycerides and the emulsifier is lecithin.

6. The suppository of claim 1 wherein the excipient and the $CaNa_2EDTA$ are present in approximately equal quantities.

7. The suppository of claim 1 comprising about 100 mg to about 1.2 gm of $CaNa_2EDTA$.

8. The suppository of claim 1 comprising about 600 mg of the excipient and about 600 mg of $CaNa_2EDTA$.

9. The suppository of claim 1 having a length of about 2-3 centimeters and a weight of about 1-2 g.

10. The suppository of claim 1 wherein the $CaNa_2EDTA$ comprises micron to nanosize particles.

11. A suppository for use in chelating heavy metals in a living being comprising:
   i. an EDTA containing compound, said EDTA compound being substantially micron to nanosized particles,
   ii. excipients comprising from 65% to 80% triglycerides, and
   iii. a carrier comprising one or more of glycerin, glyceryl monopalmitate, glyceryl monostearate, hydrogenated coconut oil fatty acids, cocoa butter, and fatty acids.

12. A system for use in chelating heavy metals in a living being comprising:
   i. calcium disodium ethylenediaminetetraacetate (CaN$_2$EDTA),
   ii. from 65% to 80% triglycerides as an excipient, and
   iii. a carrier comprising one or more of glycerin, glyceryl monopalmitate, glyceryl monostearate, hydrogenated coconut oil fatty acids, cocoa butter, and fatty acids.

* * * * *